United States Patent [19]

Moore

[11] Plant 4,657

[45] Mar. 3, 1981

[54] MINIATURE ROSE PLANT

[76] Inventor: Ralph S. Moore, 2519 E. Noble Ave., Visalia, Calif. 93277

[21] Appl. No.: 57,494

[22] Filed: Jul. 13, 1979

[51] Int. Cl.[3] ..... A01H 5/00

[52] U.S. Cl. ..... Plt./9

[58] Field of Search ..... Plt./9

*Primary Examiner*—Robert E. Bagwill
*Assistant Examiner*—James R. Feyrer

[57] ABSTRACT

The subject of the present disclosure is a new and distinct variety of miniature rose plant characterized by pink buds and flowers of distinctive form and further identified by the neat compact plant habit.

1 Drawing Figure

1

The present invention relates to a new and distinct variety of hardy, dwarf, bush type rose plant of the miniature class; the variety being primarily characterized—as to novelty—by soft to medium pink buds and flowers which in general color effect are similar to Eleanor, miniature (U.S. Plant Pat. No. 2,175).

The variety is further characterized by:

The unique shape of buds and flowers.

An abundance of bloom, with flowers borne singly or several to the stem in loose cluster.

Light sweet fragrance.

A plant which is vigorous, of rounded somewhat spreading shape with small semi-glossy (to matt) foliage with pointed leaflets; the buds and flowers being similar in form and size to the pollen parent, Fire Princess (miniature—U.S. Plant Pat. No. 3,084).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Fairy Moss—miniature (U.S. Plant Pat. No. 3,082) as the seed parent and Fire Princess—miniature (U.S. Plant Pat. No. 3,084), as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Janice Tellian.

Flowers borne: Singly and several together (3 to 5) on slender, wirey stems.

2

Quantity of bloom: Abundant both outside and in greenhouse.

Bud:

*Peduncle.*—Medium length; slender but sturdy; erect; medium to light green; hairs—usually none; thorns—none.

*Before calyx breaks, size.*—Small. Form long: pointed with several soft, very short hairs and numerous foliaceous apendages on surface of bud; with foliaceous parts extending beyond the tip of the bud equal to one-half or more of its length. Color—medium green.

*As calyx breaks, color.*—Light to medium pink—near Carmine Rose 621 to 621/1 or similar. Opening: opens well in all weather.

Bloom:

*Size when fully open.*—Small, averaging about 35–40 mm (1½").

*Petalage.*—Very double—averaging about 50 petals, arranged regularly plus several (often up to 20) petaloids.

*Form.*—Cupped at first, becoming more rounded and high centered, with petals rolled loosely outward, and later at maturity rounded, with petals remaining in similar shape and position. Open flowers do not show stamens.

Petals: Medium thickness; satiny on inside and on outside surface.

*Shape.*—Outside petals, broad lanceolate with acute tip and wedge shape base; intermediate—broad lanceolate with acute tip; inside—lanceolate with acute tip.

Color: (A) Half open flower from a plant grown in plastic house (June 1979).

*Outside petal.*—Outside surface—near Carmine Rose 621/1 becoming slightly deeper toward base and with very small near white area at base. Inside surface—near Carmine Rose 621/1 becoming a shade near Azalea Pink 618/1 on basal ⅓ of petal and with small near white or greenish area at base.

*Intermediate petal.*—Outside surface—near Carmine Rose 621 becoming lighter near base. Inside surface—near Carmine Rose 621 becoming lighter near base.

*Inner petal.*—Outside surface—same as intermediate petal; inside surface—same as intermediate petal.

Color: (B) New, fully open flower from a plant grown in plastic house (same date).

*Outside petal.*—Outside surface—near Carmine Rose 621/1 with small whiteish area at base. Inside surface—near Carmine Rose 621/1 becoming lighter toward base.

*Intermediate petal.*—Outside surface—near Carmine Rose 621/1 or 621/3. Inside surface—near Carmine Rose 621/2.

*Inner petal.*—Outside surface—similar to intermediate petal. Inside surface—similar to intermediate petal. General color effect; newly opened flowers—color is lively shade of soft pink. Three days open—color similar to newly opened flowers. Behavior—opens well in all weather. Spent petals tend to hand on for a time, then old flowers drop (separates at base of peduncle). Flower longevity (May 1978)—plant in pot 4–5 days or longer. Cut flowers at living room temperature 3–4 days or longer.

Reproductive organs:

*Stamens.*—Few—usually none.

*Filaments.*—Usually none.

*Anthers.*—Occasional—usually none.

*Pollen.*—None.

*Pistils.*—Average number.

*Styles.*—Fairly even; very short; bunched; color—reddish.

*Ovaries.*—All enclosed in calyx.

*Hips.*—None.

*Sepals.*—Permanent; spear shaped; tend to remain flat under flower.

*Seed.*—None.

Foliage:

*Leaves.*—Compound of five or seven leaflets—usually five; quite small; leathery; semi-glossy to matt.

*Leaflets.*—Shape: broad lanceolate; nearly oval; apex acute; base rounded or rounded acute. Margin serrate. Color: medium green; new growth—normal (medium) green. Rachis: medium strength; upper side may have several tiny short hairs or prickles, grooved; underside may have several thorns—1 to 5 but no hairs. Stipules: medium long; narrow to medium width; short length narrow points which turn out usually at about 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Fairly numerous; slender; curved slightly downward; color: brown. Prickles—none; hairs—none.

*Branches.*—Color: light to medium green. Thorns: moderate amount; medium length; slender; curved slightly downward. Medium to short oval base. Prickles: none. Hairs: none.

*Young shoots.*—Color: light to medium green. Thorns; moderate amount, slender; nearly straight; color: greenish to brownish.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described characterized by buds and flowers which are a soft to medium shade (or shades) of pink, the buds and flowers resembling Eleanor (U.S. Plant Pat. No. 2,175) in color and Fire Princess (U.S. Plant Pat. No. 3,084) in form and size, the buds and flowers having a distinct and unique appearance as compared to other pink miniature roses, said flowers being very double, of rounded form; and further characterized by a plant which is vigorous and compact with abundant small foliage and easy to propagate from soft wood cuttings or by budding, with an abundance of flowers borne singly or several to the stem in loose clusters.

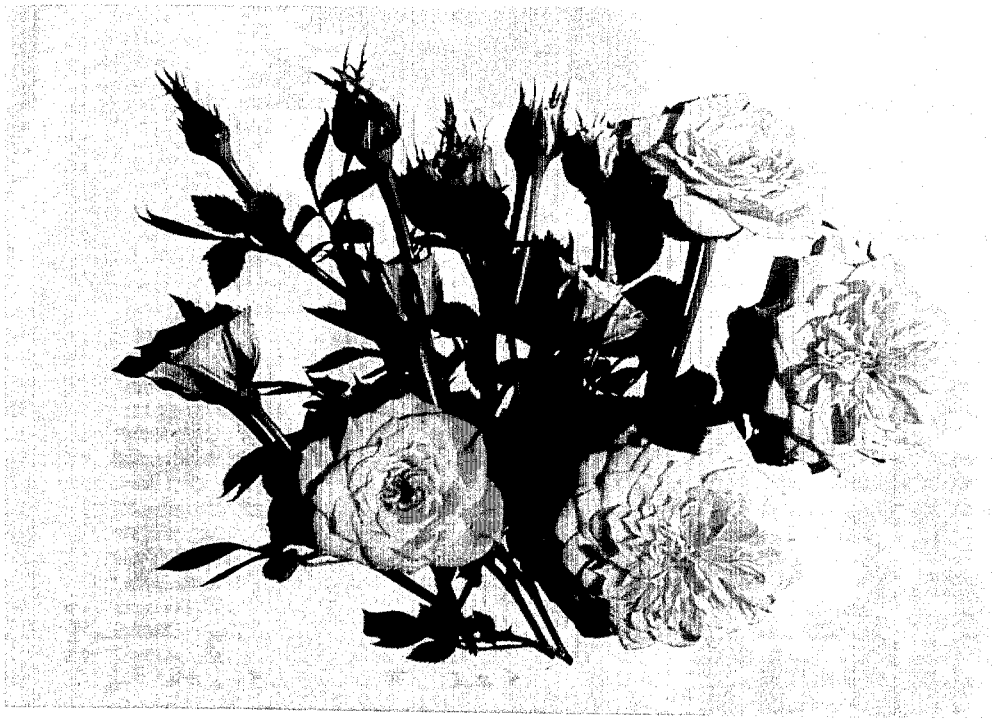

* * * * *